(12) United States Patent
Cole et al.

(10) Patent No.: US 8,366,679 B2
(45) Date of Patent: Feb. 5, 2013

(54) SELF FILLING INJECTION DEVICE (75) Inventors: John P. Cole, Alpharetta, GA (US);
Tesfaye H. Gutema, Alpharetta, GA (US)

(73) Assignee: Cole Isolation Technique, LLC, Alpharetta, GA (US)

( * ) Notice: Subject to any disclaimer, the term of this patent is extended or adjusted under 35 U.S.C. 154(b) by 703 days.

(21) Appl. No.: 12/386,496

(22) Filed: Apr. 16, 2009

(65) Prior Publication Data
US 2010/0268168 A1 Oct. 21, 2010

(51) Int. Cl.
*A61M 5/31* (2006.01)
*A61M 5/32* (2006.01)
*A61M 5/20* (2006.01)

(52) U.S. Cl. ............... 604/192; 604/207; 604/131

(58) Field of Classification Search .......... 604/192, 604/207, 131, 212–231, 135, 404, 408, 233
See application file for complete search history.

(56) References Cited

U.S. PATENT DOCUMENTS

| 2,156,023 | A | * | 4/1939 | McKay | 604/184 |
|---|---|---|---|---|---|
| 2,625,264 | A | * | 1/1953 | Edwards, Jr. | 206/364 |
| 3,016,897 | A | * | 1/1962 | Kendrick | 604/186 |
| 5,034,003 | A | * | 7/1991 | Denance | 604/117 |
| 5,106,374 | A | * | 4/1992 | Apperson et al. | 604/140 |
| 5,395,326 | A | * | 3/1995 | Haber et al. | 604/90 |
| 5,709,667 | A | * | 1/1998 | Carilli | 604/198 |
| 5,938,646 | A | * | 8/1999 | Carter | 604/317 |
| 6,056,728 | A | * | 5/2000 | von Schuckmann | 604/207 |
| 6,077,253 | A | * | 6/2000 | Cosme | 604/263 |
| 6,302,864 | B1 | * | 10/2001 | Nowosielski | 604/65 |
| 6,565,538 | B2 | * | 5/2003 | Quinn et al. | 604/181 |
| 7,041,084 | B2 | * | 5/2006 | Fojtik | 604/181 |
| 2002/0183698 | A1 | * | 12/2002 | Quinn et al. | 604/227 |
| 2003/0073902 | A1 | * | 4/2003 | Hauschild et al. | 600/431 |
| 2008/0275422 | A1 | * | 11/2008 | Ross | 604/408 |
| 2010/0145283 | A1 | * | 6/2010 | Walker et al. | 604/192 |

* cited by examiner

*Primary Examiner* — Kevin C Sirmons
*Assistant Examiner* — Michael J Anderson
(74) *Attorney, Agent, or Firm* — Berkeley Law & Technology Group, LLP (57) ABSTRACT

Embodiments of methods, apparatuses, devices and systems associated with injection devices are disclosed.

20 Claims, 10 Drawing Sheets

SELF FILLING INJECTION DEVICE

FIELD

Embodiments relate to the field of injection devices.

INFORMATION

Injection devices, such as hypodermic needles, have a variety of applications in the medical and veterinary fields, including but in no way limited to, in the surgical field. In addition, such injection devices may be used under a variety of circumstances. Accordingly, advances in such injection devices may be desirable or advantageous.

BRIEF DESCRIPTION OF DRAWINGS

Subject matter is particularly pointed out and distinctly claimed in the concluding portion of the specification. Claimed subject matter, however, both as to organization and method of operation, together with objects, features, and advantages thereof, may best be understood by reference of the following detailed description when read with the accompanying drawings in which:

DETAILED DESCRIPTION

In the following detailed description, numerous specific details are set forth to provide a thorough understanding of claimed subject matter. However, it will be understood by those skilled in the art that claimed subject matter may be practiced without these specific details. In other instances, methods, procedures, components, or the like that would be known by one of ordinary skill have not been described in detail so as not to obscure claimed subject matter.

Reference throughout this specification to "one embodiment" or "an embodiment" means that a particular feature, structure, or characteristic described in connection with the embodiment is included in at least one embodiment of claimed subject matter. Thus, the appearances of the phrase "in one embodiment" or "an embodiment" in various places throughout this specification are not necessarily all referring to the same embodiment. Furthermore, the particular features, structures, or characteristics may be combined in one or more embodiments.

Embodiment relate to a device for allowing a user to administer an injection while using one hand. In addition, embodiments relate to a device that may likewise be filled automatically, under some circumstances, using only one hand. For example, an injectible fluid may be supplied to a device by a bottle or a bag in an at least somewhat continuous manner. In at least one embodiment, a typically available disposable syringe may be used with such a self filing injection device.

Figure 1:
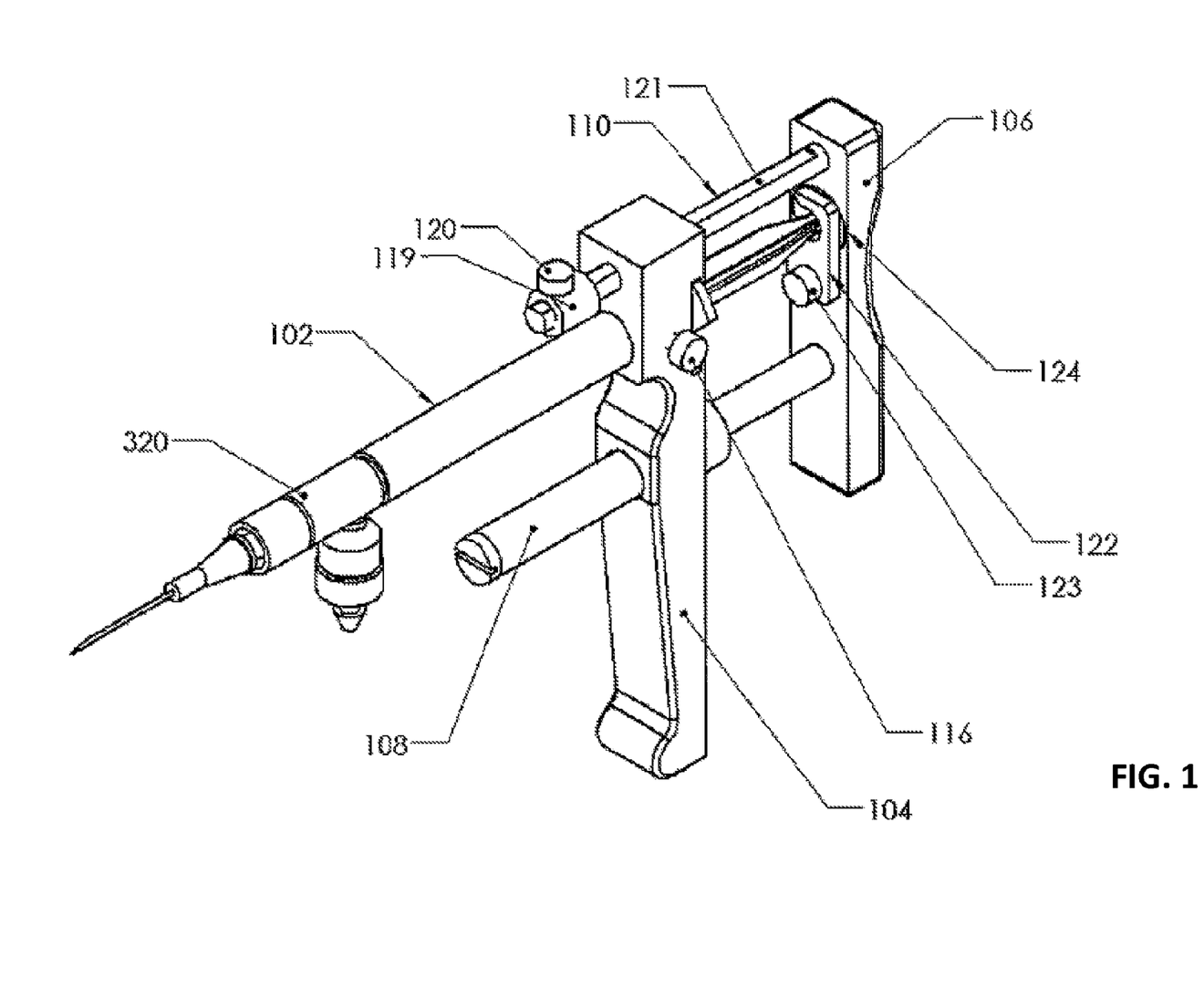
FIG. 1 depicts a perspective view of a Self Filling Injection Device in accordance with an embodiment.
Figure 2:
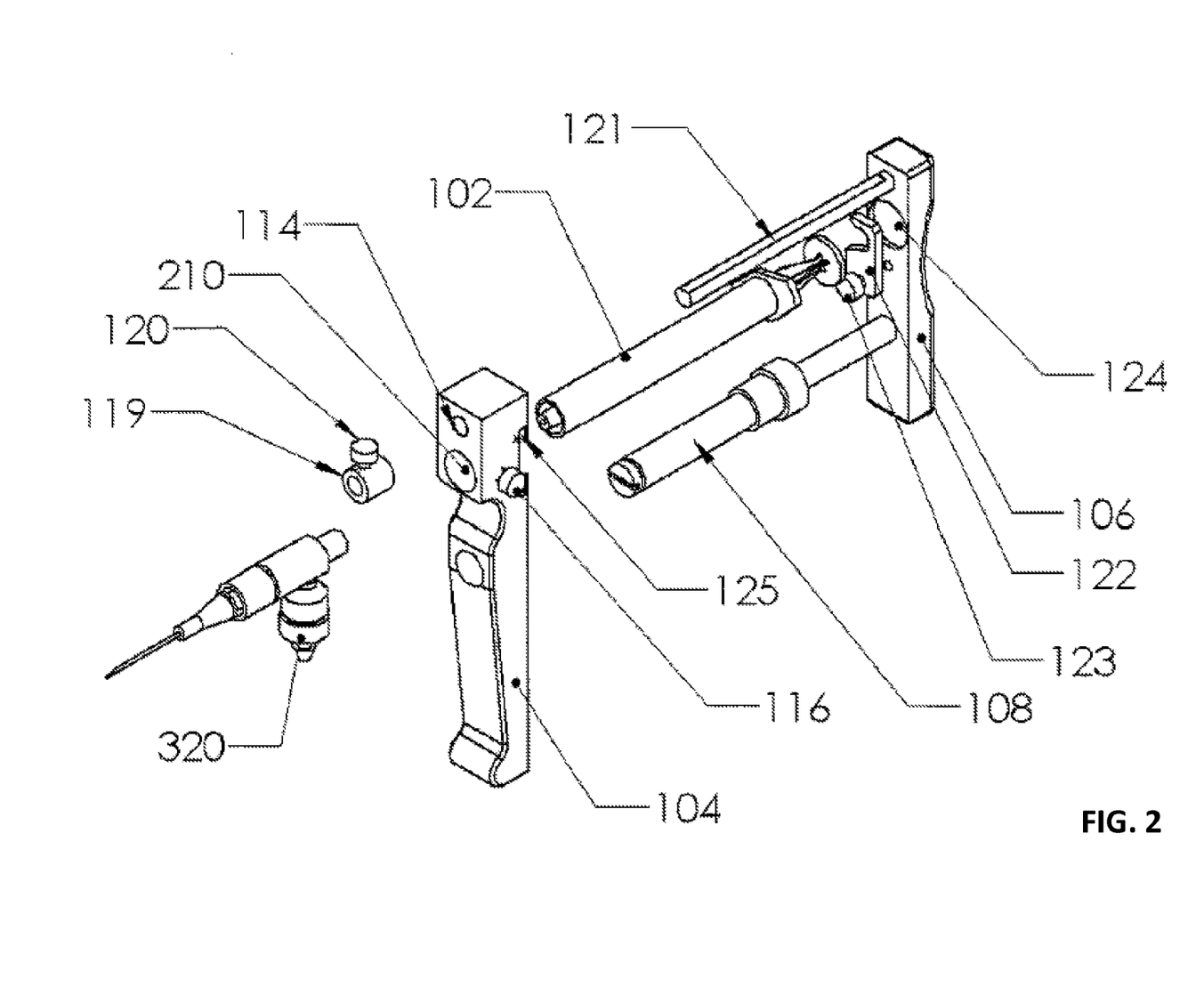
FIG. 2 depicts an exploded view of one or more aspects of the Self Filing Injection Device shown in FIG. 1.
Figure 3:
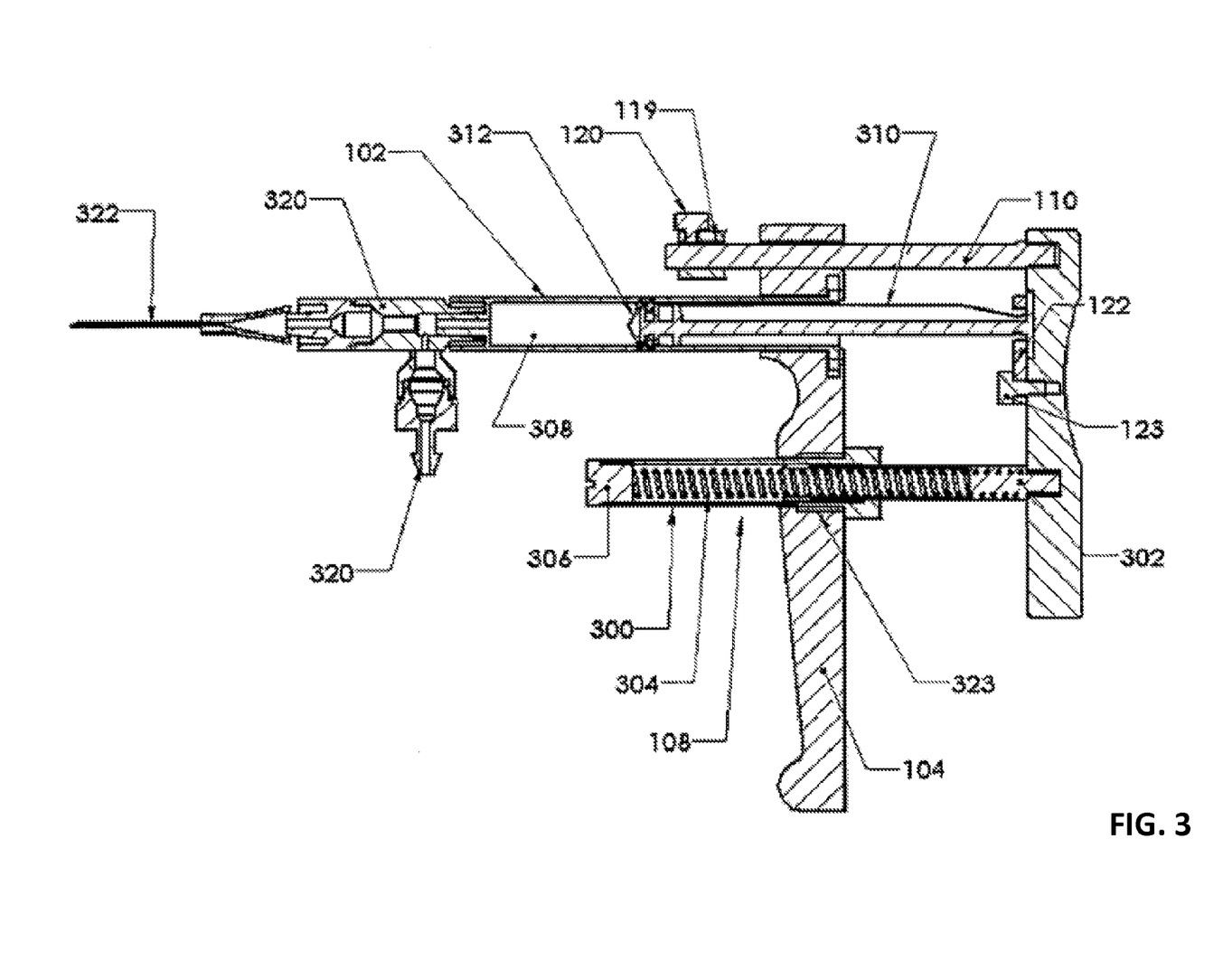
FIG. 3 depicts a section view of the Self Filling Injection Device in FIG. 1.

FIG. 1 depicts a perspective view of a device 100, such as a self filing injection device in accordance with an embodiment. With regard to FIG. 1, device 100 may comprise a syringe assembly 102, a front handle 104, a back handle 106, a spring assembly 108, and a guide pin 110. The main components of this device are shown in FIG. 1, FIG. 2 and FIG. 3. As shown in FIG. 3, a spring assembly 108 may comprise a biasing mechanism operable to supply fluid pressure to one or more portions of device 100, such as from manually, mechanically, or otherwise stored energy. In this particular embodiment, spring assembly 108 may comprise a first biasing portion, such as a female type spring guide 300, a second biasing portion, such as a male type spring guide 302, a spring 304, and a set screw or a blind flange 306. In at least one embodiment, male type spring guide 302 may be at least partially inserted into female type spring guide 300 along with spring 304 and at least partially closed with flange 306. In this example, male type guide 302 may be operably coupled to female type guide 300 such that male type guide 302 slides freely if spring 304 may be compressed or extended. In at least one embodiment, this subassembly forms spring assembly 108. In this embodiment, spring assembly 108 may be at least partially fixedly connected to back handle 106, such as by threading a portion of male spring guide 302 into back handle 106. In at least one embodiment, spring assembly 108 may, in addition, be coupled to front handle 104. In this example, spring assembly 108 specifically the female type guide 300 may be fixedly coupled to front handle 104 by threading 323 or by using one or more thumb screws or set screws. In an embodiment, guide pin 110 may be operably coupled to back handle 106, such as by screwing into back handle 106 and may be operable to freely slide through guide hole 114. Dose adjust sleeve 119 may be operably coupled to guide pin 110 by using a set screw 120 or by threading (not shown). In at least one embodiment, guide hole 114 may be positioned within a portion of front handle 104. It should, however, be noted that these are merely illustrative examples relating to an injection device and that claimed subject matter is not limited in this regard.

As shown in FIG. 3 the syringe assembly 102 may comprise a barrel 308, a sliding plunger 310, and a seal boot 312. In at least one embodiment, sliding plunger 310 may be operatively coupled to back handle 106, such as by inserting a flange on sliding plunger 310 into a recess formed in back handle 106. In one embodiment, lock plate 122 may be rotated around and stopped by syringe plunger 310. In this position, the lock plate 122 may limit the motion of flange of syringe plunger 310 and hold it in the recess 124 provided in back handle 106.

In at least on embodiment, syringe assembly 102, back handle 106, spring assembly 108, and guide pin 110 may be operatively coupled to front handle 104 at least in part by inserting syringe assembly 102, into a bore hole 210 (shown in FIG. 2) of front handle 104, spring assembly 108 into a lower bore hole of front handle 104, and inserting guide pin 110 into guide hole 114 of front handle 104. In this example, syringe 102 may be fixed in place at least in part by rotating a flange of syringe 102 in slot 124 provided in front handle 104 and/or using thumb screw 116. Thumb screw 116 may be threaded into one or more threads in front handle 104. In this example, thumb screw 116 may apply a force, such as friction, to at least in part prevent syringe 102 from sliding relative to front handle 106. It should, however, be noted that this is merely an illustrative example relating to an injection device and that claimed subject matter is not limited in this regard.

In an embodiment, spring assembly 108 may be coupled in a relatively fixed position at least in part by threading 323 between female spring guide 300 and front handle 104 as shown in FIG. 3. In another embodiment, a thumb screw or a set screw, or some other fixing device may be used to hold spring box 108 relative to front handle 104. In an embodiment, dose adjust sleeve 119 may be operably coupled to guide pin 110 by using a set screw 120 or by threading (not shown). One face of dose adjust sleeve 119 may be used as a stopper against the front handle 104. The position of dose adjust sleeve 119 may determine the relative position of syringe plunger 310 which in turn determines a dose in syringe 102. The position of dose adjust sleeve 119 may be changed by loosening set screw 120 tightened on flat 121 provided on guide pin 110, moving dose adjust sleeve 119 to a new position and re-tightening set screw 120. At least in part as a result of a new position, the syringe plunger 310 may be moved back and forth to define a new dose in the syringe barrel 308. In at least one embodiment, a desirable position for dose adjust sleeve 119 may be determined by looking at a scale (not shown) provided on syringe barrel 308 that may be aligned with the tip of boot 312 assembled on syringe plunger 310. In another embodiment, a scale (not shown) may be provided on guide pin 110 to correspond a desirable amount of fluid contained in syringe barrel 308. It should, however, be noted that these are merely illustrative examples relating to an injection device and that claimed subject matter is not limited in this regard.

As shown in FIG. 3, a valve or valves, such as a dual checkvalve 320, such as one or more available dual checkvalves may be coupled to an end of syringe 102. For example, dual checkvalve 320 may comprise an integral stainless steel, plastic body, thermoplastic body, or the like, consisting of an inlet ball valve or port and an outlet ball valve or port. In this example, the balls in the valves may loaded with springs so that, in conjunction they allow such balls to open and close depending on whether such a valve is subjected to a suction or an injection process. In this example, the inlet valve may be connected to a hose extending to a Fluid bag or bottle (not shown). Furthermore, in this example the outlet valve may be connected to a hypodermic needle 322. Though, again, these are merely illustrative examples relating to an injection device and claimed subject matter is not limited in this regard.

In an embodiment, device 100 may under some circumstances be held such that the forefinger may be inserted into a gap 118 on the front handle 104 between syringe 102 and spring assembly 108, while one or more other fingers may be placed under spring assembly 108. For example, in an initial state, spring 304 may be in an extended position. In this example, a user may initiate a forward motion, such as by pushing back handle 106 towards from handle 104 from a starting position. Such a motion may result in spring 304 being compressed and syringe plunger 310 being moved forward. During such forward motion, the outlet valve of dual checkvalve 320 may open while the inlet valve closes under the spring forces acting on the balls on the two sides. In this example, if a user release pressure applied to back handle 106, spring 304 may push back handle 106 away from front handle 104. In this example, back handle 106 may likewise pull with it male type spring guide 302, syringe plunger 310, and guide pin 110 to the initial position. During this motion, the outlet valve closes the inlet valve opens under the spring forces acting on the balls on the two sides. In this case, fluid may be drawn or sucked into syringe assembly 102 from a fluid bag or bottle by a suction force created in syringe barrel 308. In this example, if back handle 106 is pushed towards front handle 104 again, the outlet valve opens and the inlet valve closes under the spring forces acting on the balls on the two sides. Thus the fluid content syringe barrel 308 may be discharged through hypodermic needle 322. In this example, under some circumstances, hypodermic needle 322 that may be injected into a subject or patient. Though, again, these are merely illustrative examples relating to an injection device and claimed subject matter is not limited in this regard.

In this embodiment, a syringe 102 may be removed or replaced at least in part by loosening thumb screws 120 and 116 and withdrawing back handle 106 backwards as shown in FIG. 2. In this example, the syringe, guide pin 121 and spring assembly 108 may be detached from front handle 104 at least in part by sliding them backwards. In this example, front handle 104, back handle 106, guide pin 121 and spring assembly 108 may be cleaned and sterilized after use, while syringe assembly 102 may, under some circumstances, be disposed of after use.

In an embodiment, various components of device 100 may be manufactured from a variety of materials, such as stainless steel, plastics, aluminum, titanium, combinations thereof, or the like. The various parts may be manufactured by machining, molding, forming, cutting, casting, powder deposition or a combination of any such processes.

The operation of the devices described above may be performed by means of a manual force, a solenoid, a pneumatic, hydraulic or an actuator of some means. The dose discharged from the syringe may also, under some circumstances, be controlled by limiting a stroke of the movable parts of the actuating devices.

Figure 4:
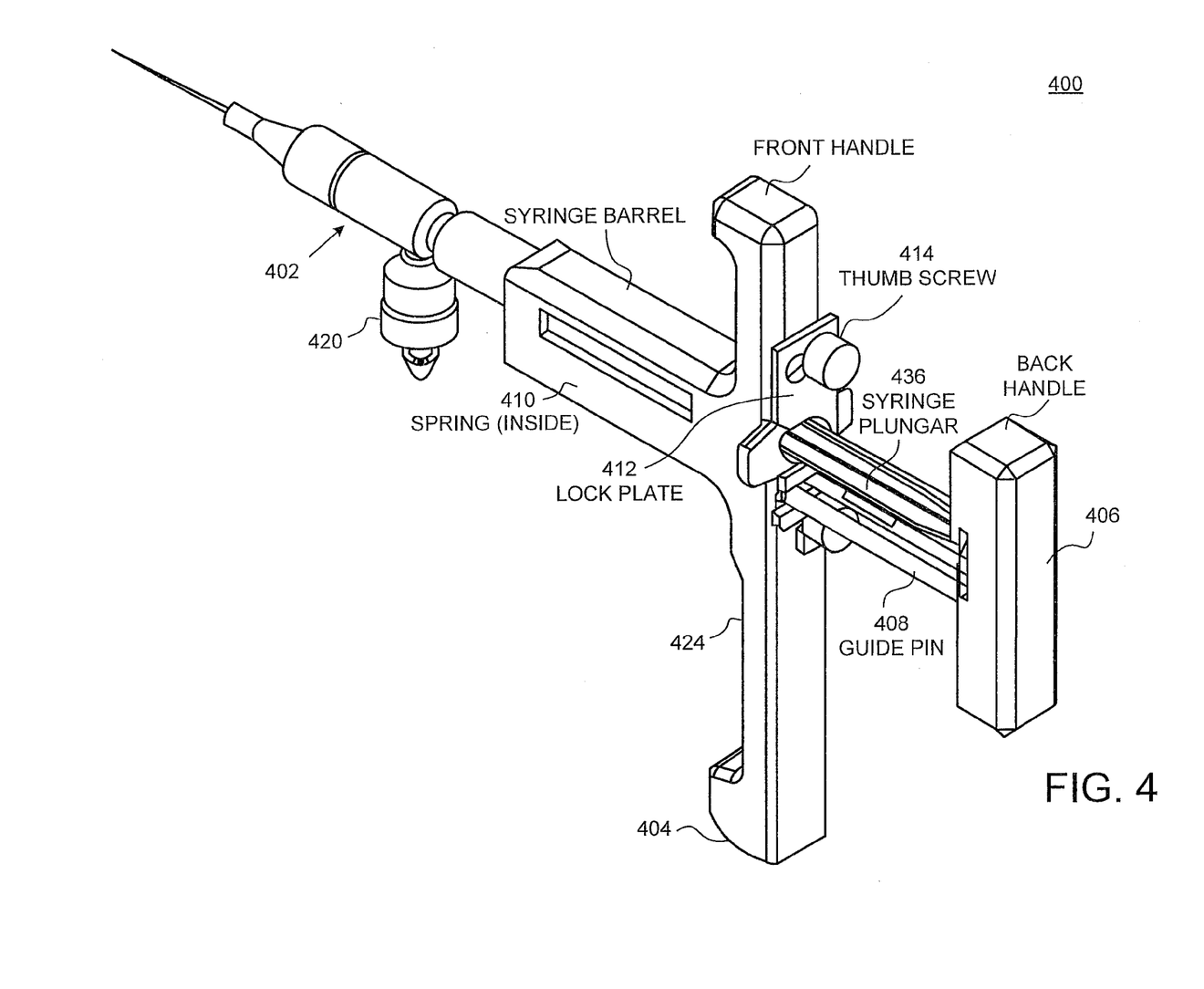
FIG. 4 depicts a perspective view of a Self Filling Injection Device in accordance with another embodiment.
Figure 5:
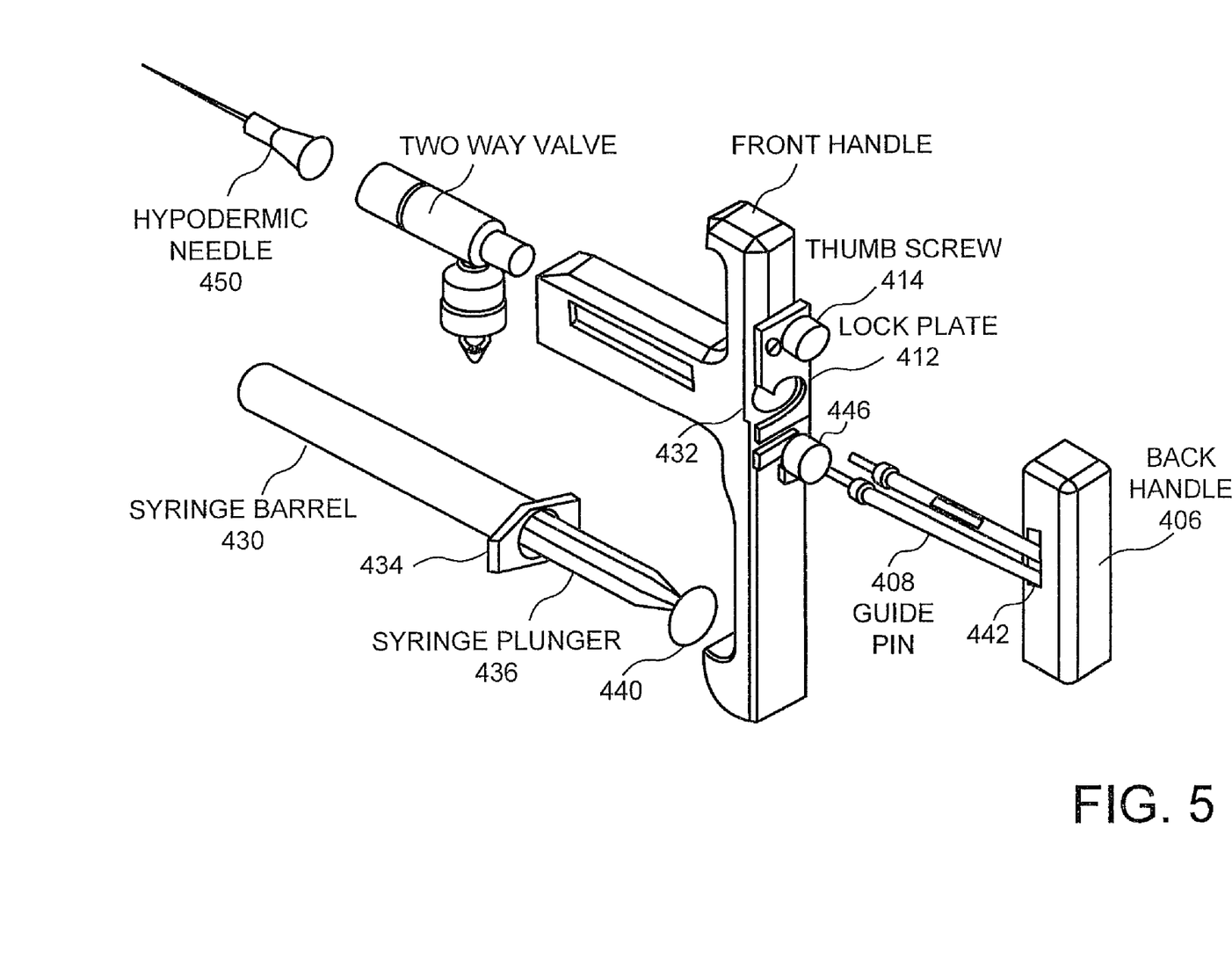
FIG. 5 depicts an exploded view of one or more aspects of the Self Filling Injection Device shown in FIG. 1.
Figure 6:
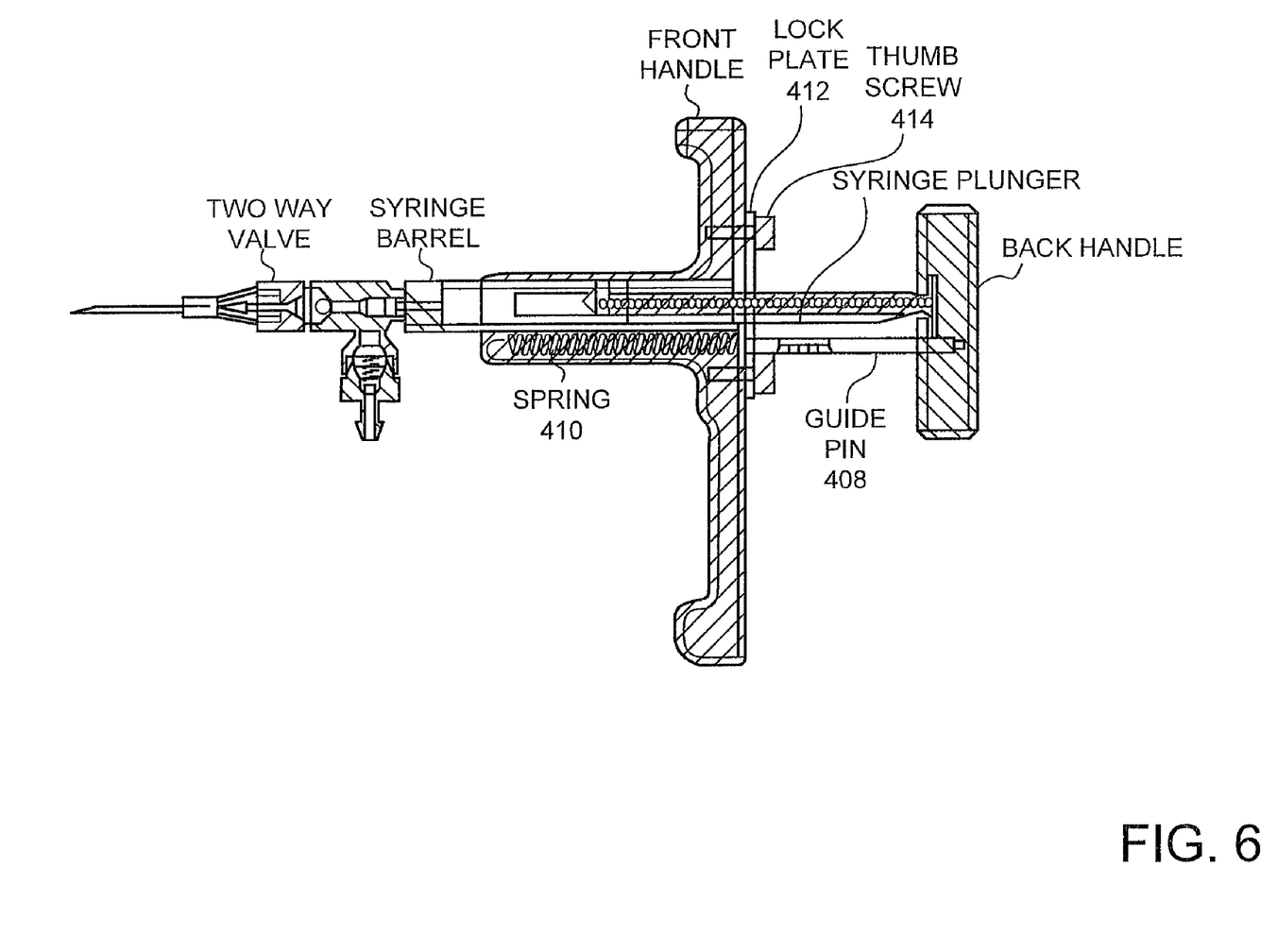
FIG. 6. depicts a section view of the Self Filling Injection Device in FIG. 4.

FIGS. 4-6 depict various views of another device 400, such as another self filling injection device in accordance with another embodiment. Device 400 may comprise a syringe assembly 402, a front handle 404, a back handle 406, guide pin 408, spring 410 (shown in FIG. 6), lock plate 412, thumb screw 414, and a dual checkvalve 420. In this embodiment, a standard syringe assembly may be used to contain and deliver one or more injectible fluids. In this particular embodiment, spring 410 and guide pin assemblies may be contained in front handle 404. In at least one embodiment, front handle 404 may have an at least partially T shape. In this example, a vertical portion of front handle 404 may be used at least in part for a user to hold device 400. For example, vertical portion 422 (above a horizontal portion) may be used to grip with a forefinger while a vertical portion 424 (below the horizontal portion) may be held one or more remaining fingers. In this embodiment, a horizontal portion of front handle 404 may be adapted to at least partially house a syringe barrel 430 (shown in FIG. 5), one or more springs, such as spring 410, and guide pin 408. In this embodiment, front handle 404 may further comprise a bore hole oriented in a longitudinal manner at least in part for at least partially housing syringe barrel 430. In addition, front handle 404 may include a recess 432 sized or shaped to receive a flange 434 of the syringe at to at least partially prevent syringe plunger 436 from rotating about a longitudinal axis of the syringe. In this embodiment, a syringe assembly 432 may be inserted in to the bore hole in front handle 404 until syringe flange 434 is fitted in recess 432 of front handle 404. In this embodiment, a plunger flange 440 may be inserted into a slot 442 positioned on, or formed in, back handle 406

In an embodiment, once syringe 430 and guide pins 408 (or additional guide pins as may be desirable) are inserted into front handle 406, a lock plate 412 may be pushed in and may be manipulated to at least partially fix the syringe and guide pins in a position. In an embodiment, the guide pin(s) may be at least partially fixedly coupled with back handle 406 and may be pushed against spring 430, such as in response to a user actuation of device 400. In one embodiment, back handle 406 may be pushed until a shoulder on the guide pins is pushed past the back surface of front handle 404. In this position, lock plate 412 may be rotated around thumb screw 412 until a groove of lock plate 412 may be aligned with a lower thumb screw 446. In this position, the lock plate 412 may limit the motion of guide pins and also may hold the syringe flange against the back surface of the front handle 406. Though, again, these are merely illustrative examples relating to an injection device and claimed subject matter is not limited in this regard.

In an embodiment, dual checkvalve 420 may be coupled to a distal end of the syringe assembly 402. In this embodiment, dual checkvalve 420 may be an integral body consisting of an inlet valve and an outlet valve. In this example, the inlet valve may be connected to a hose extending to a fluid bag or bottle (not shown). The outlet valve at the distal end may be connected to a hypodermic needle 450 in a manner similar to that described above with regard to FIGS. 1-3. In this embodiment, syringe plunger 436 may be mechanically coupled to back handle 406. In this embodiment, a force fat least in part from spring 410 may return syringe plunger 436 to a starting position.

A bag or a bottle containing the fluid may be connected to the inlet valve by means of hoses (not shown). The outlet valve may be coupled to a needle to be inserted into the subject by means of a luer lock mechanism. In the initial state, spring 410 may be in an extended or starting position. A forward motion may be initiated by a user, such as by a user pushing back handle 406 towards front handle 404 from a starting position. In doing so, spring 410 may be compressed and syringe plunger 436 may be moved forward. During this forward motion, the outlet valve of dual checkvalve 420 may open and the inlet valve may close under the spring forces acting on the balls on the two sides. If a user releases the pressure applied to back handle 406, spring 430 may push back on back handle 406. Back handle 406 may in turn pull with it a syringe plunger 436 and guide pin 408 to an initial or staring position. During this motion, the outlet valve of dual checkvalve 420 may close while the inlet valve opens under the spring forces acting on the balls on the two sides. In this example, an injectible fluid may be drawn or sucked from the Fluid bag or bottle by the suction created in syringe barrel 430 at least in part by the movement of syringe plunger 436. If back handle 406 is pushed again, the outlet valve or dual checkvalve 420 may open and the inlet valve may close under the spring forces acting on the balls on the two sides. Thus the fluid content in syringe barrel 430 may be discharged through hypodermic needle 450. A Hypodermic needle that may be injected into a subject may be attached to the outlet port of the valve by a luer connection. In at least one embodiment, there may be a fluid connection between the needle, the valve and the syringe barrel. However, it should be noted that these are merely illustrative examples relating to an injection device and that claimed subject matter is not limited in this regard.

In this embodiment, if it is desirable to remove the syringe, the appropriate thumb screws may be loosened, the lock plate may be moved to a side and rotated around the upper thumb screw until it clears the Barrel flange and the shoulders on the Guide pins. In this example, the syringe may be pushed back by the springs. In addition, the plunger flange may be removed from the back handle and the syringe may be removed and, if appropriate, disposed of.

In an embodiment, various components of device 400 may be manufactured from a variety of materials, such as stainless steel, plastics, aluminum, titanium, combinations thereof, or the like. The various parts may be manufactured by machining, molding, forming, cutting, casting, powder deposition or a combination of any of the processes.

The operation of the devices described above may be performed by means of a manual force, a solenoid, a pneumatic, hydraulic or an actuator of some means. The dose discharged from the syringe may also, under some circumstances, be controlled by limiting a stroke of the movable parts of the actuating devices.

Figure 7:
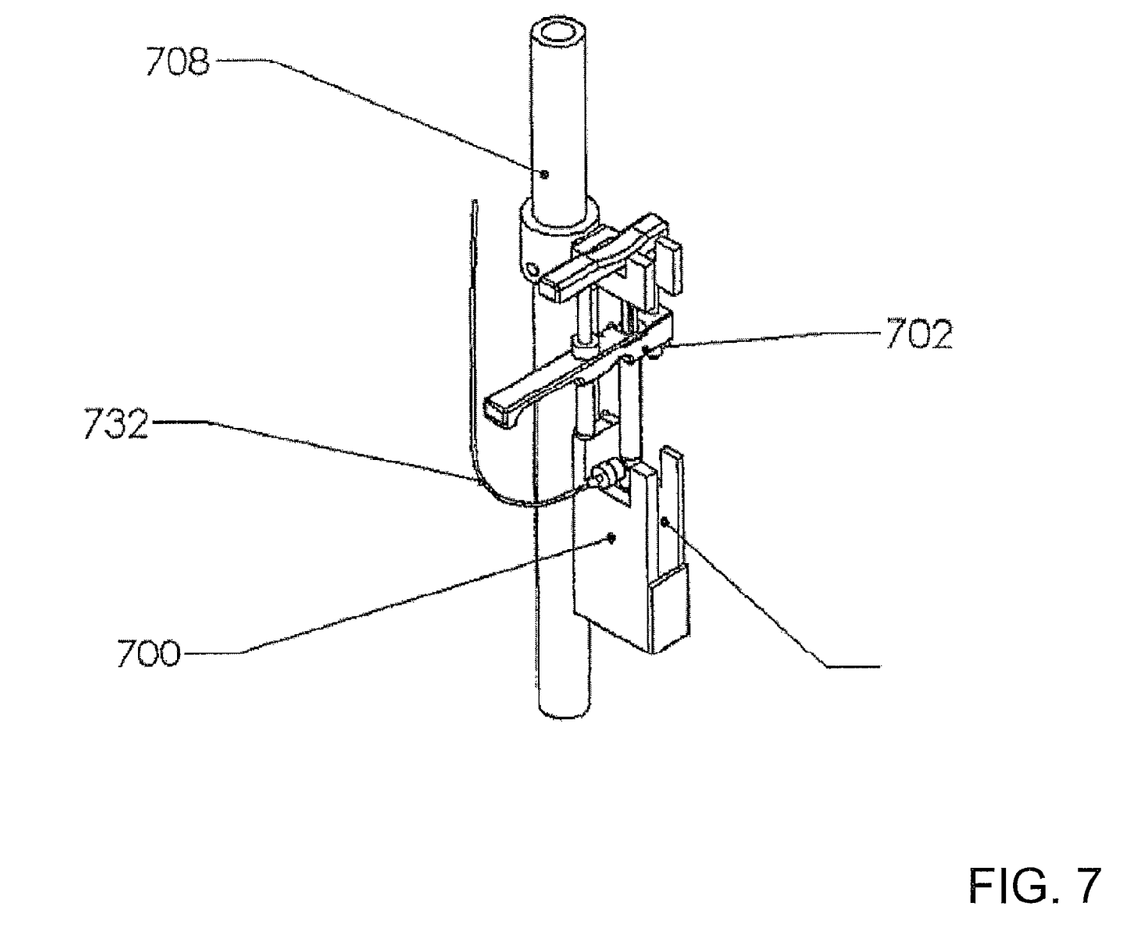
FIG. 7 depicts a perspective view of a Safe Injection Device Holder assembled on an IV pole with a Self Filling Injection Device in place in accordance with an embodiment.
Figure 8:
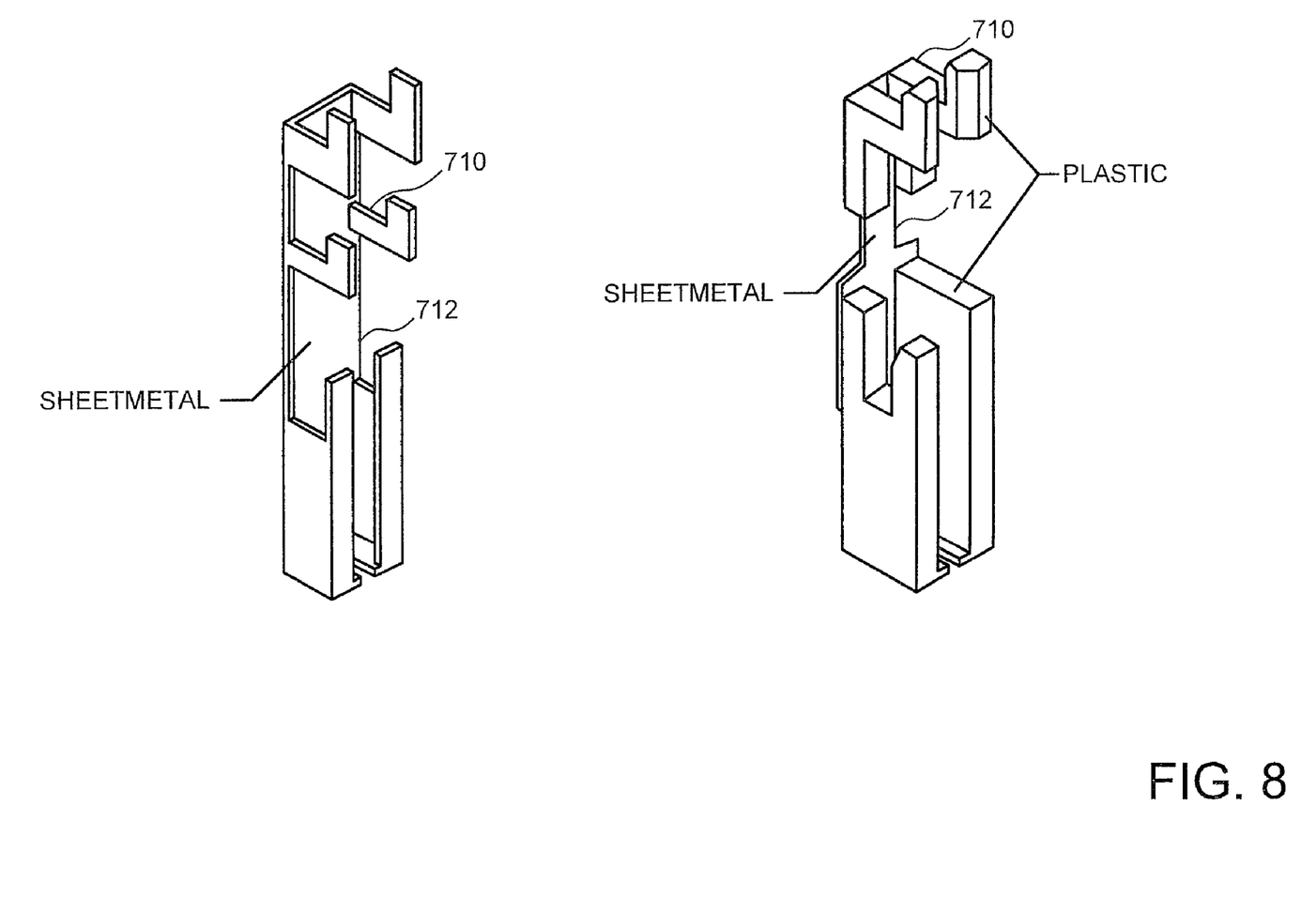
FIG. 8 depicts a perspective view of a Safe Injection Device Holder in accordance with an embodiment.

FIGS. 7 and 8 depict a device holder for an injection device. In a surgery room it may be desirable for sharps, such as devices including hypodermic needles, to be placed in a safe place to protect the personnel. In addition, it may be desirable for a needle in an injection device to be placed such that the needle may be safe from contamination and the sharp tip of the needle should not be accessed by people working around the device. In at least one embodiment, an injection device holder 700 may accordingly be desirable or advantageous. Injection device holder 700 may be used to mount or store an injection device, such as, but not limited to, those described above, when such devices are not currently being used. Injection device holder 700 may be shaped and positioned such that it allows relatively easy placing and removal of an injection device 702. In one embodiment, injection device holder 700 may be at least partially fixedly mounted to a pole 708, such as a pole for holding one or more IV bags, such as by hanging the bags or bottles on hooks secured to the pole with one or more screws. To place injection device 702 in the injection device holder 700, injection device 702 may be positioned such as by moving a back handle so that it may be slid vertically downwards into injection device holder 700 until it is supported by the shoulder provided on the holder. In this embodiment, a back handle of injection device 702 may be positioned to rest on an upper ledge 710 (shown in FIG. 8) and the front handle in a middle portion 712. In at least one embodiment, a hose 732 extending out of a valve inlet port of injection device 702 may extend out towards a top part of the IV pole hanger (not shown). The needle may be contained in all sides except one and can not be reached easily. To remove, one may hold the front handle and first pull upwards and then away from the holder.

In at least one embodiment, injection device 702 may be reached for and grabbed with one hand without using assistance from a second hand. In addition, injection device holder 700 may be manufactured from a variety of materials, such as stainless steel sheet metal, plastics, aluminum sheet metal, titanium, combinations thereof, or the like. The various parts may be manufactured by machining, molding, forming, cutting, casting, powder deposition or a combination of any such processes.

Figure 9:
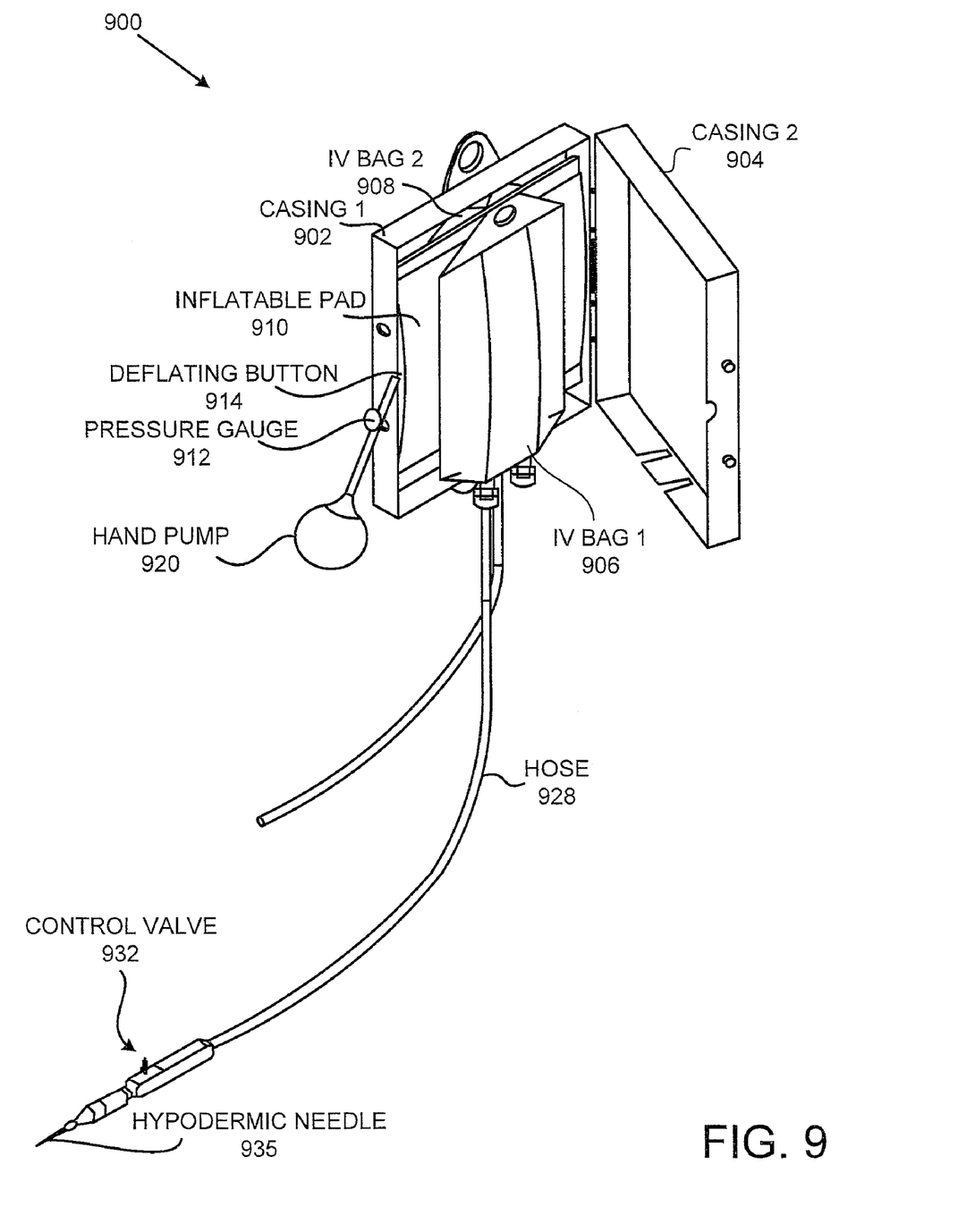
FIG. 9 depicts a perspective view of the assembly of an Inflatable Injection Device

FIG. 9 depicts an inflatable injection device 900 in accordance with an embodiment. Inflatable injection device 900 may comprise a casing, such as a casing including a first casing portion 902 and a second casing portion 904. In an embodiment, casing portions 902 and 904 may each comprise a plastic or metal part, hinged together and may, under some circumstances include a locking mechanism and one or more slots. In an embodiment, one or two IV bags, such as IV bags 906 and 908, may be placed within a portion of first casing portion 902 or second casing portion 904. In at least one embodiment, a biasing mechanism, such as inflatable pad 910, one or more mechanically actuated plates, an electrically actuated solenoid, a pneumatically or hydraulically actuated biasing mechanism, or the like, may be positioned between the two IV bags or between an IV bag and a portion of one of the casing portions. As used herein, a biasing mechanism may refer to one or more mechanisms at least in part operable to apply one or more pressures. For example, a biasing mechanism may, under some circumstances be operable to applying a suction pressure at least in part to suck one or more fluids into an area. For another example, a biasing mechanism may, under some circumstances apply a pressure at least in part to evacuate one or more fluids from an area. In one embodiment, inflatable pad 910 may be connected to a pressure gauge 912 by means of a tube. In addition, inflatable injection device 900 may include a deflation valve or button positioned on or in tubing between inflatable pad 910 and pressure gauge 912. An IV administration set (hose end) may be connected to the port of the IV bag or bags and the hose may extend out to a valve. In this embodiment, the valve may mainly consist of a hose clamp and a non return valve. The hose coming from the IV bags may pass through a Hose clamp and may be connected to one end of the non return valve. The distal end of the non return valve may have a luer connection that may be connected to a hypodermic needle.

Figure 10:
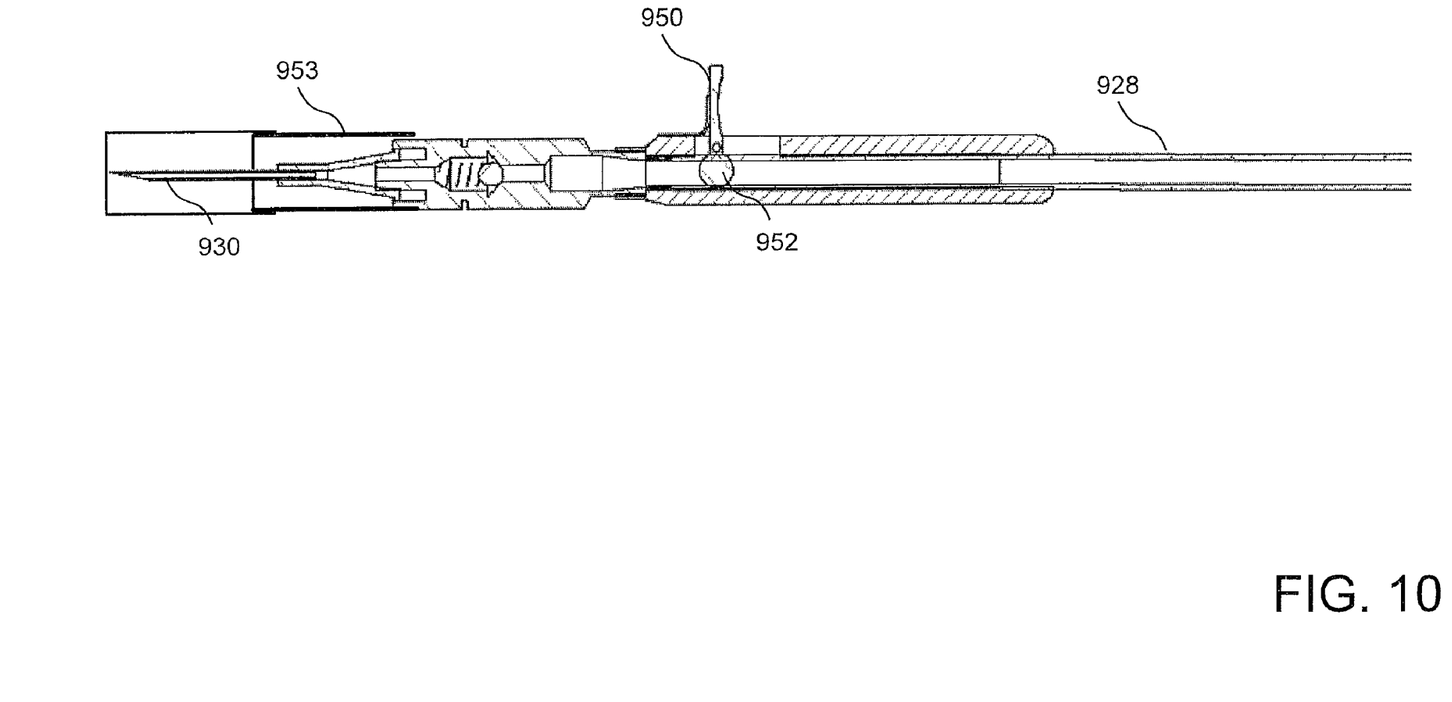
FIG. 10 depicts a section view of a control valve of the Inflatable Injection Device shown in FIG. 9.

In addition, inflatable injection device 900 may include a pumping mechanism, such as hand pump 920 or an electric pump (not shown). If hand pump 920 is actuated one or more times, inflatable pad 910 may fill with one or more gases and apply pressure to IV bags 906 and 908. In at least one embodiment, a fluid pressure in Inflatable pad 910 may be indicated at least in part by pressure gauge 912. If a desirable pressure is reached, then a user may stop inflating inflatable pad 910. In this embodiment, one or more fluids within IV bags 906 and 908 may begin to fill hose 928 until it reaches hypodermic needle 930 or control valve 932. If, however, a handle 950 on the control valve 932 is actuated, such as by a user, a ball 950 pressing on hose 928 may be lifted allowing the fluid to exit through hypodermic needle 930. It should, however, be noted that these are merely illustrative examples relating to an injection device and that claimed subject matter is not limited in this regard. The device may be mounted on an IV pole with a mounting hole disposed on the casing and the valve end may be secured on a snap mechanism on the holder (not shown). Alternatively, the needle tip may be protected by using sliding retractable shield 953. In an embodiment, sliding retractable shield 953 may comprise an at least partially retractable shield mounted onto the valve body. In addition, sliding retractable shield 953 may extend and cover at least a portion of the needle when not in use and retract back and expose the needle part when an injection is to be given.

In the preceding description, various aspects of claimed subject matter have been described. For purposes of explanation, specific numbers, systems or configurations were set forth to provide a thorough understanding of claimed subject matter. However, it should be apparent to one skilled in the art having the benefit of this disclosure that claimed subject matter may be practiced without the specific details. In other instances, features that would be understood by one of ordinary skill were omitted or simplified so as not to obscure claimed subject matter. While certain features have been illustrated or described herein, many modifications, substitutions, changes or equivalents will now occur to those skilled in the art. It is, therefore, to be understood that the appended claims are intended to cover all such modifications or changes as fall within the true spirit of claimed subject matter.

The invention claimed is:

1. An apparatus, comprising:
a syringe assembly comprising a hypodermic needle;
an at least partially retractable shield to at least partially cover a portion of said hypodermic needle;
a valve operatively coupled to said hypodermic needle, wherein said valve comprises two or more ports capable of fluid communication; and
a bias mechanism operatively coupled to said valve, wherein said bias mechanism is capable of supplying fluid pressure to said two or more ports at least partially from energy stored by said bias mechanism;
wherein a fluid is capable of being drawn into said syringe assembly via at least a first of said two or more ports at least partially in response to said supplied fluid pressure comprising a suction force to be supplied by said bias mechanism.

2. The apparatus of claim 1, further comprising:
a front handle removably coupled to a syringe main body of said syringe assembly and adjustably coupled to a first bias portion of said bias mechanism, wherein said bias mechanism comprises said first bias portion and a second bias portion in slidable communication; and
a back handle removably coupled to a syringe plunger and coupled to said second bias portion, wherein said syringe plunger is in slidable communication with a syringe main body of said syringe assembly.

3. The apparatus of claim 1, wherein said valve comprises a dual checkvalve.

4. The apparatus of claim 2, wherein said bias mechanism comprises a spring loaded bias mechanism.

5. The apparatus of claim 2, further comprising:
a guide pin operatively coupled between said front handle and said back handle, wherein said guide pin is capable of maintaining a substantially parallel orientation between said front handle and said back handle; and
a dose adjusting sleeve operatively coupled to said guide pin, wherein said dose adjusting sleeve is capable of adjusting a dosage volume available to said syringe assembly.

6. The apparatus of claim 2, further comprising a mounting device to removably support at least a portion of said front handle or said back handle.

7. The apparatus of claim 6, wherein said mounting device comprises an opening to at least partially cover said hypodermic needle.

8. The apparatus of claim 6, wherein said mounting device is fixedly attached to a pole for supporting an IV bag.

9. The apparatus of claim 1, wherein said energy comprises manual energy.

10. The apparatus of claim 1, wherein said energy comprises mechanical energy.

11. An apparatus comprising:
a syringe assembly comprising a hypodermic needle;
a valve operatively coupled to said hypodermic needle, wherein said valve comprises two or more ports capable of fluid communication; and
a bias mechanism operatively coupled to said valve, wherein said bias mechanism is capable of supplying fluid pressure to said two or more ports from energy stored by said bias mechanism said bias mechanism comprising an inflatable pad operatively coupled to a pump;

a casing comprising an interior compartment, wherein said interior compartment is capable of housing a fluid bag and said inflatable pad; and a control valve comprising a housing, a channel disposed within said housing, and a hose clamp movably coupled to said housing, wherein said channel is capable of removably receiving a hose operatively coupled to said fluid bag therethrough, and wherein said hose clamp is capable of selectively closing said channel to fluid communication;

wherein a fluid is capable of being drawn into said syringe assembly via at least a first of said two or more ports at least partially in response to said supplied fluid pressure comprising a suction force to be supplied by said bias mechanism.

12. The apparatus of claim 11, wherein said valve comprises a non-return-type valve.

13. The apparatus of claim 11, further comprising a pressure gauge or a deflation device operatively coupled to said bias mechanism.

14. The apparatus of claim 11, wherein said casing comprises a base portion and a lid portion, wherein said base portion and said lid portion are capable of being removably coupled to form said interior compartment.

15. The apparatus of claim 11, wherein the supplied fluid pressure is capable of providing said fluid to said hypodermic needle.

16. The apparatus of claim 11, and further comprising at least a partially retractable shield to at least partially cover a portion of said hypodermic needle.

17. The apparatus of claim 1, wherein said bias mechanism comprising one or more mechanically actuated plates, an electrically actuated solenoid, a pneumatically or hydraulically actuated biasing mechanism, or combinations thereof.

18. An apparatus comprising:
a syringe assembly comprising a hypodermic needle;
a valve operatively coupled to said hypodermic needle, wherein said valve comprises two or more ports capable of fluid communication; and
a bias mechanism operatively coupled to said valve, wherein said bias mechanism is capable of supplying fluid pressure to said two or more ports from energy stored by said bias mechanism, wherein said bias mechanism comprises one or more mechanically actuated plates, an electrically actuated solenoid, a pneumatically or hydraulically actuated biasing mechanism, or combinations thereof;
a casing comprising an interior compartment, wherein said interior compartment is capable of removably housing a fluid bag and said bias mechanism; and
a control valve comprising a housing, a channel located in said housing, and a hose clamp movably coupled to said housing, wherein said channel is capable of removably receiving a hose operatively coupled to a fluid bag therethrough, and wherein said hose clamp is capable of selectively closing said channel to fluid communication;
wherein a fluid is capable of being drawn into said syringe assembly via at least a first of said two or more ports at least partially in response to said supplied fluid pressure comprising a suction force to be supplied by said bias mechanism.

19. The apparatus of claim 18, and further comprising an at least partially retractable shield to at least in part cover a portion of said hypodermic needle.

20. The apparatus of claim 1, wherein said fluid is capable of being drawn out of said syringe assembly via at least a second of said two or more ports at least partially in response to said supplied fluid pressure comprising an injection force supplied by said bias mechanism.

* * * * *